United States Patent [19]

Chan

[11] 4,230,875
[45] Oct. 28, 1980

[54] FUNGICIDAL, MITICIDAL AND OVICIDAL ALKOXYCARBONYLALKYL-SUBSTITUTED AND CARBAMYLALKYL-SUBSTITUTED N-HALOALKYLTHIOSULFONAMIDES

[75] Inventor: David C. K. Chan, San Francisco, Calif.

[73] Assignee: Chevron Research Company, San Francisco, Calif.

[21] Appl. No.: 921,385

[22] Filed: Jul. 3, 1978

Related U.S. Application Data

[62] Division of Ser. No. 734,858, Oct. 22, 1976, Pat. No. 4,112,237.

[51] Int. Cl.$^2$ .............................................. C07C 145/02
[52] U.S. Cl. ...................................... 560/12; 560/121; 560/125; 560/150; 260/556 A; 260/556 AR
[58] Field of Search ................. 560/12, 121, 125, 150; 260/556 A, 556 AR

[56] References Cited

U.S. PATENT DOCUMENTS

| | | | |
|---|---|---|---|
| 2,713,058 | 7/1955 | Kittleson | 260/556 AR |
| 3,285,929 | 11/1966 | Klauke | 260/556 AR |
| 3,678,017 | 7/1972 | Shelton | 260/556 AR |
| 3,703,500 | 11/1972 | Nast | 260/556 AR |

OTHER PUBLICATIONS

Govindachari, Indian Journal of Chem., 9, pp. 537–538, (1971).

*Primary Examiner*—Natalie Trousof
*Assistant Examiner*—Michael Shippen
*Attorney, Agent, or Firm*—D. A. Newell; T. G. DeJonghe; R. J. Suyat

[57] ABSTRACT

Fungi, mites and mite eggs are killed by applying thereto sulfonamides of the formula

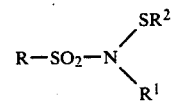

wherein R and R$^1$ individually are alkyl, cycloalkyl, aryl, carbamylalkyl, or alkoxycarbonylalkyl and R$^2$ is haloalkyl, with the proviso that one R or R$^1$ group is carbamylalkyl or alkoxycarbonylalkyl.

12 Claims, No Drawings

FUNGICIDAL, MITICIDAL AND OVICIDAL ALKOXYCARBONYLALKYL-SUBSTITUTED AND CARBAMYLALKYL-SUBSTITUTED N-HALOALKYLTHIOSULFONAMIDES

This is a division of application Ser. No. 734,855, filed Oct. 22, 1976 now U.S. Pat. No. 4,112,237.

BACKGROUND OF THE INVENTION

U.S. Pat. No. 3,178,447, issued to G. K. Kohn on Apr. 13, 1965, discloses the fungicidal activity of N-polyhaloethylthio-substituted aryl- and alkanesulfonamides.

U.S. Pat. No. 2,779,788, issued to H. Gysin et al on Jan. 29, 1957, discloses fungicidal N-trichloromethylthio-substituted chloromethanesulfonamides.

U.S. Pat. No. 3,925,555, issued to I. Okuda et al on Dec. 9, 1975, discloses the control of mites with chloromethanesulfonamides.

DESCRIPTION OF THE INVENTION

The compounds of the invention are represented by the formula

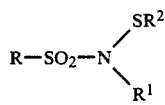

(I)

wherein R and $R^1$ individually are alkyl of 1 to 6 carbon atoms; cycloalkyl of 5 to 8 carbon atoms substituted with up to 2 alkyl of 1 to 4 carbon atoms; phenyl substituted with up to 2 of the same or different substituents selected from fluoro, chloro, bromo, iodo, trifluoromethyl, trichloromethyl, tribromomethyl, or alkyl of 1 to 4 carbon atoms; alkoxycarbonylalkyl of 2 to 6 carbon atoms; carbamylalkyl of 1 to 6 carbon atoms; N-alkylcarbamylalkyl of 2 to 6 carbon atoms; or N,N-dialkylcarbamylalkyl of 3 to 6 carbon atoms and $R^2$ is haloalkyl of 1 to 2 carbon atoms and of 1 to 5 fluoro, chloro, bromo or iodo, with the proviso that one R or $R^1$ is alkoxycarbonylalkyl, carbamylalkyl of 1 to 6 carbon atoms, N-alkylcarbamylalkyl of 2 to 6 carbon atoms, or N,N-dialkylcarbamylalkyl of 3 to 6 carbon atoms.

Representative alkyl groups which R and $R^1$ may represent include methyl, ethyl, propyl, isopropyl, butyl, hexyl, etc. Representative cycloalkyl and alkylcycloalkyl groups which R and $R^1$ may represent include cyclopentyl, 3-methylcyclopentyl, cyclohexyl, 2,4-dimethylcyclohexyl, 4-ethylcyclohexyl, cycloheptyl, cyclooctyl, 5-methylcyclooctyl, etc. Representative aryl groups which R and $R^1$ may represent include phenyl; substituted phenyl such as 4-fluorophenyl, 2-chlorophenyl, 4-iodophenyl, 2,4-dibromophenyl, 2,4-dimethylphenyl, 2-methyl-4-chlorophenyl, trifluoromethylphenyl, etc.

Representative $R^2$ groups are fluoromethyl, chloromethyl, iodomethyl, dichloromethyl, dibromomethyl, trifluoromethyl, trichloromethyl, 1,1,1-trichloroethyl, 1,1,2,2-tetrachloroethyl, 1,2,2,2-tetrachloroethyl and pentachloroethyl.

Representative alkoxycarbonylalkyl R and $R^1$ groups are methoxycarbonylmethyl, ethoxycarbonylmethyl, n-butoxycarbonylmethyl, 1-(methoxycarbonyl)ethyl and 3-(methoxycarbonyl)propyl. Representative carbamylalkyl R and $R^1$ groups are carbamylmethyl, carbamylethyl, N-alkylcarbamylalkyl of 2 to 6 carbon atoms, such as N-methylcarbamylmethyl and N-ethylcarbamylmethyl, and N,N-dialkylcarbamylalkyl of 3 to 6 carbon atoms, such as N,N-dimethylcarbamylmethyl and 1-(N,N-diethylcarbamyl)ethyl.

Preferred alkyl R or $R^1$ groups are alkyl of 1 to 3 carbon atoms. Preferred cycloalkyl R or $R^1$ groups are cycloalkyl of 5 to 6 carbon atoms substituted with up to 2 alkyl of 1 to 4 carbon atoms. Preferred aryl R or $R^1$ groups are phenyl and phenyl-substituted with 1 to 2 of the same or different substituents selected from fluoro, chloro, bromo, trifluoromethyl or alkyl of 1 to 4 carbon atoms.

The preferred alkoxycarbonylalkyl R and $R^1$ groups are alkoxycarbonylmethyl and 1-(alkoxycarbonyl)ethyl of 2 to 4 carbon atoms. The preferred carbamylalkyl R and $R^1$ groups are N,N-dialkylcarbamylalkyl of 3 to 6 carbon atoms. The preferred $R^2$ groups are haloalkyl of 1 to 2 carbon atoms and of 1 to 5 chloro or bromo. The most preferred $R^2$ groups are trichloromethyl and tetrachloroethyl.

One class of preferred compounds of formula (I) is that wherein one R or $R^1$ group is alkoxycarbonylalkyl, carbamylalkyl, N-alkylcarbamylalkyl or N,N-dialkylcarbamylalkyl and the other R or $R^1$ group is alkyl, cycloalkyl or aryl as defined above.

Another preferred class of compounds is that wherein R is alkoxycarbonylalkyl and $R^1$ is phenyl substituted with up to 2 of the same or different substituents selected from fluoro, chloro, bromo, trifluoromethyl or alkyl of 1 to 4 carbon atoms.

Another preferred class of compounds is that wherein R is alkyl of 1 to 6 carbon atoms, cycloalkyl of 5 to 8 carbon atoms substituted with up to 2 alkyl of 1 to 4 carbon atoms, or phenyl substituted with up to 0.2 of the same or different substituents selected from fluoro, chloro, bromo, trifluoromethyl, or alkyl of 1 to 4 carbon atoms and $R^1$ group is alkoxycarbonylalkyl of 2 to 6 carbon atoms.

Representative compounds of the invention include:
N-methoxycarbonylmethyl-N-(1,1,2,2-tetrafluoroethylthio)-methanesulfonamide N-n-propoxycarbonylmethyl-N-(trichloromethylthio)-4-chlorophenylsulfonamide N-[1-(methoxycarbonyl)ethyl]-N-(1,1,2,2-tetrabromoethylthio)isopropanesulfonamide N-ethoxycarbonylmethyl-N-(fluoromethylthio)-2-chloroethanesulfonamide N-ethyl-N-(1,1,2,2-tetrachloroethylthio)-methoxycarbonylmethanesulfonamide N-chloromethyl-N-(2,2,2-triiodoethylthio)-(1-methoxycarbonyl)ethanesulfonamide N-butoxycarbonylmethyl-N-(dichloromethylthio)cyclohexanesulfonamide N-cyclohexyl-N-(1,1,2,2-tetrachloroethylthio)ethoxycarbonylmethanesulfonamide, N-methoxycarbonylmethyl-N-(1,1,2,2-tetrachloroethylthio)-4-chlorophenylsulfonamide, N-2-fluorophenyl-N-(1,1,2,2-tetrachloroethylthio)-methoxycarbonylmethanesulfonamide, N-2-trifluoromethylphenyl-N-(1,1,2,2-tetrachloroethylthio)carbamylmethanesulfonamide, and N-methoxycarbonylmethyl-N-(trichloromethylthio)-methylcarbamylmethanesulfonamide.

The compounds of the invention are prepared by sulfenylating a sulfonamide of the formula $R-SO_2-NHR^1$ (II), wherein R and $R^1$ have the same significance as previously defined, with a haloalkylsulfenyl chloride of the formula R²SCl (III) wherein R² has the same significance as previously defined. The sulfenylation reaction is generally conducted by reacting substantially equimolar quantities of the sulfonamide (II) and the sulfenyl chloride (III) in the liquid phase in the presence of an acid acceptor. Suitable acid acceptors are organic amines such as pyridine compounds, e.g., pyridine or alpha-picoline, and lower trialkylamines, e.g., triethylamine or tributylamine, and inorganic alkali metal hydroxides, e.g., sodium hydroxide or potassium hydroxide. Generally, at least one mol of acid acceptor is employed for each mol of sulfenyl chloride (III). The reaction is normally conducted in an inert liquid diluent, e.g., organic solvents such as chlorinated hydrocarbons.

The sulfenylation reaction may be conducted in the presence of catalytic amounts of a quaternary ammonium salt. Generally, amounts of quaternary ammonium salt per mol of the sulfenyl chloride (III) reactant vary from about 0.01 to 0.3, although amounts from 0.05 to 0.2 mol per mol of the sulfenyl chloride (III) are preferred. Suitable quaternary ammonium salts are tetraalkylammonium halides wherein the alkyl has 1 to 6 carbon atoms and the halide is fluoro, chloro, bromo or iodo, e.g., tetramethylammonium chloride or tetrabutylammonium bromide.

The sulfenylation reaction is conducted at a temperature of 0° C. to the boiling point of the diluent, although temperatures between 0° C. and 100° C. are preferred. The reaction is conducted at or above atmospheric pressure. The reaction time will, of course, vary depending on the reaction temperature and the particular reactants employed. Generally, the reaction is completed within one-half to 24 hours. The product (I) is isolated and purified by conventional procedures such as extraction, filtration, crystallization and chromatography.

The sulfenylation reaction may also be conducted with an alkali metal salt of the sulfonamide (II) and the haloalkyl sulfenyl chloride (III) by conventional procedures.

MITE OVICIDAL ACTIVITY

The compounds of the invention have been found to be useful and effective for the killing of mite eggs. Some compounds of the invention are also useful and effective for the killing of mites.

Any conventional techniques or methods can be employed for contacting mites or mite eggs with an effective miticidal or ovicidal amount of the compounds of the invention. Like most agricultural chemicals, they are not usually applied full strength, but are generally incorporated with conventional biologically inert extenders or carriers normally employed for facilitating dispersion of active ingredients for agricultural chemical applications, recognizing the accepted fact that the formulation and mode of application may affect the activity of a material. The toxicants of this invention may be applied as sprays, dusts, or granules to the mites or mite eggs, their environment or hosts susceptible to mite attack. They may be formulated as granules of large particle size, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from 5-80% toxicant and the rest inert material which includes dispersing agents, emulsifying agents, and wetting agents. The powder may be applied to the soil as a dry dust or preferably as a suspension in water. Typical carriers include fuller's earth, kaolin clays, silicas, and other highly absorbent, readily wet, inorganic diluents. Typical wetting, dispersing, or emulsifying agents used in agricultural formulations include, for example, the alkyl and alkylaryl sulfonates and sulfonates and their sodium salts; alkylamide sulfonates, including fatty methane taurides, alkylaryl polyether alcohols, sulfated higher alcohols, and polyvinyl alcohols; polyethylene oxides; sulfonated animal and vegetable oils; sulfonated petroleum oils; fatty acid esters of polyhydric alcohols and the ethylene oxide addition products of such esters; and the addition products of long chain mercaptans and ethylene oxide. Many other types of useful surface active agents are available in commerce. The surface active agent, when used, normally comprises from one percent to fifteen percent by weight of the pesticidal composition.

Dusts are freely flowing admixtures of the active ingredient with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about fifty microns. A typical dust formulation useful herein contains 75% silica and 25% of the toxicant.

Useful liquid concentrates include the emulsifiable concentrates, which are homogeneous liquid or paste compositions which are readily dispersed in water to other dispersant, and may consist entirely of the toxicant with a liquid or solid emulsifying agent, or may also contain a liquid carrier, such as xylene, heavy aromatic naphthas, isophorone, and other nonvolatile organic solvents. For application these concentrates are dispersed in water or other liquid carrier, and normally applied as a spray to the area to be treated.

The percentages by weight of the toxicant may vary according to the manner in which the composition is to be applied and the particular type of formulation, but in general comprises 0.5% to 95% of the toxicant by weight of the pesticidal composition.

The compositions may be formulated and applied with other active ingredients, including nematocides, insecticides, fungicides, bactericides, plant growth regulators, fertilizers, etc. In applying the chemical an effective amount and concentration of the toxicants of this invention is, of course, employed.

FUNGICIDAL UTILITY

The compounds of the invention are also useful for controlling fungi, particularly plant fungal infections caused by *Botrytis cinerea*, leaf blights caused by organisms such as *Pythrium ultimum, Helminthosporum sativum, Fusarium moniliforme, Rhizoctonia solani, Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus and the particular compound of the invention. The fungicides of the invention are generally incorporated with conventional biologically inert extenders or carriers normally employed for facilitating dispersion of active fungicidal compounds. Thus, the fungicides of the invention may be formulated and applied as granules, as powdery dusts, as wettable powders, as emulsifiable concentrates, as solutions, or as any of several other known types of formulations, depending on the desired mode of application.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

Example 1—Preparation of N-methoxycarbonylmethyl-N-trichloromethylthiobenzenesulfonamide A 47.5 g (0.6 mol) sample of pyridine was added dropwise to a stirred and cooled (ice bath) slurry of 53.0 g (0.3 mol) benzenesulfonyl chloride and 37.7 g (0.3 mol) glycine methyl ester hydrochloride in 500 ml dichloromethane. The reaction mixture was then allowed to warm to 25° C. and was stirred for about 16 hours. The reaction mixture was diluted with 250 ml water, the organic layer was separated, washed with water, washed with 10% aqueous hydrochloric acid solution, washed with water, dried over magnesium sulfate and evaporated to give 36.5 g N-(methoxycarbonylmethyl)-benzenesulfonamide, which crystallized as a colorless solid melting at 62°–63° C. A 3.5 g (0.035 mol) sample of triethylamine was added dropwise to a solution of 8 g (0.035 mol) N-methoxycarbonylmethyl)benzenesulfonamide and 6.5 g (0.035 mol) trichloromethylsulfenyl chloride in 150 ml dichloromethane. The reaction mixture was then stirred at about 25° C. for about 1 hour, washed with water, dried over magnesium sulfate and evaporated to give 7.5 g of N-methoxycarbonylmethyl-N-trichloromethylthiobenzenesulfonamide, which crystallized as a colorless solid melting at 61°–62° C. The compound is tabulated in Table I as Compound No. 1.

Example 2—Preparation of N-methoxycarbonylmethyl-N-(1,1,2,2-tetrachloroethylthio)cyclohexanesulfonamide A 1.2 g (0.03 mol) sample of sodium hydroxide in 1.2 ml water was added dropwise to a solution of 6.5 g (0.03 mol) N-(methoxycarbonylmethyl)cyclohexanesulfonamide, 7.0 g (0.03 mol) 1,1,2,2-tetrachloroethylsulfenyl chloride, 0.5 g. triethylbenzylammonium chloride in 100 ml dichloromethane. The resulting reaction mixture was stirred at about 25° C. for 3 hours, washed with water, dried over magnesium sulfate and evaporated under reduced pressure to give an oil residue. The residue was chromatographed through silica gel. Elution with 10% ethyl ether/hexane gave 2.5 g of the product as an oil. Elemental analysis for $C_{11}H_{17}Cl_4NO_4S_2$ showed: %Cl, calc. 32.7, found 32; %S, calc. 14.8, found 15.1. The product is tabulated in Table I as Compound No. 2.

Example 3—Preparation of N-[1-(ethoxycarbonyl)ethyl]-N-(1,1,2,2-tetrachloroethylthio)cyclohexanesulfonamide A 9.2 g (0.05 mol) sample of cyclohexanesulfonyl chloride was added dropwise to a solution of 7.7 g (0.05 mol) of the hydrochloride salt of ethyl 2-aminopropionate and 4 g (0.05 mol) sodium hydroxide in 14 ml water and 100 ml acetonitrile. The reaction mixture was heated under reflux for 24 hours, cooled, filtered and evaporated under reduced pressure to give the crude product mixture. The product mixture was diluted with dichloromethane, washed with water, dried over magnesium sulfate and dried under reduced pressure to give the crude N-[1-(ethoxycarbonyl)ethyl]cyclohexanesulfonamide product.

A 1-g (0.02 mol, 50% in mineral oil) of sodium hydride was added in small portions to 5 g of the crude sulfonamide product prepared above. The resulting reaction mixture was then added slowly to a stirred solution of 4.7 g (0.02 mol) 1,1,2,2-tetrachloroethylsulfonyl chloride in 100 ml dichloromethane. The reaction mixture was stirred for an additional hour and evaporated under reduced pressure to give a dark residue. The residue was diluted with dichloromethane, washed with water, dried over magnesium sulfate and evaporated under reduced pressure to give the crude product mixture. The product mixture was chromatographed through silica gel with 10% ethyl ether/90% hexane elution to give 2.2 g of N-[1-(ethoxycarbonyl)ethyl]-N-(1,1,2,2-tetrachloroethylthio)cyclohexanesulfonamide, as an oil. Elemental analysis for $C_{13}H_{21}Cl_4NO_4S_2$ showed: %Cl, calc. 30.8, found 33.0; %S, calc. 12.9, found 13.4. The product is tabulated in Table I as Compound No. 3.

Example 4—Preparation of N-phenyl-N-(1,1,2,2-tetrachloroethylthio)-methoxycarbonylmethylsulfonamide A slurry of 217 g (2 mols) methyl chloroactate and 252 g (2 mols) sodium sulfite in 500 ml water was stirred and heated under reflux for about 2 hours. The resulting solution was allowed to stand at about 25° C. for 56 hours and then evaporated under reduced pressure to give solid residue. The residue was washed with acetone and dried under vacuum at 80°–90° C. to give crude sodium methoxycarbonylmethylsulfonate salt.

The sodium methoxycarbonylmethylsulfonate salt was added in small portions to a stirred solution of 840 ml (9.14 mols) phosphorus oxychloride. The resulting mixture was then heated at 80°–100° C. for about 5 hours and allowed to cool overnight. The reaction mixture was filtered, the filtered solid was washed with dichloromethane and the filtrate distilled under reduced pressure to remove the dichloromethane and excess phosphorus oxychloride. The resulting oil residue was distilled through a short Vigreaux column to give 226.8 g (65.7% yield) of methoxycarbonylmethylsulfonyl chloride, as a yellow oil, b.p. 79°–80° C. (0.5 mm Hg).

A 10-g (0.058 mol) sample of methoxycarbonylmethylsulfonyl chloride was added dropwise to a cooled (−8° C.) solution of 10.4 g (0.116 mol) aniline in 200 ml dichloromethane. The reaction mixture was allowed to warm to 25° C. and was stirred for 1 hour. The resulting N-phenyl-(methoxycarbonylmethyl)sulfonamide product was filtered and washed with ether. After drying, the product melted at 76°–77° C.

A 6.1 g (0.06 mol) sample of triethylamine was added dropwise to a cooled (ice bath) solution of 13.8 g (0.06 mol) N-phenyl-(methoxycarbonylmethyl)sulfonamide and 14.1 g (0.06 mol) 1,1,2,2-tetrachloroethylsulfenyl chloride in 200 ml dichloromethane. The reaction mixture was then allowed to warm to 25° C., stirred for 3 hours at 25° C., washed with water, dried over magnesium sulfate, and evaporated under reduced pressure to give the product mixture. The product mixture was chromatographed through 300 g silica gel. Elution with 60% chloroform/40% hexane gave the N-phenyl-N-(1,1,2,2-tetrachloroethylthio)-methoxycarbonylmethyl)sulfonamide product, as a colorless solid, m.p. 95°-96° C. This product is tabulated in Table I as Compound No. 4.

Example 5—N,N-(dimethylcarbamylmethyl)-N-(1,1,2,2-tetrachloroethylthio)benzenesulfonamide To a stirred solution of 23.0 gm (0.0949 mol) N,N-dimethylcarbamylmethylbenzenesulfonamide and 2.5 gm (0.01 mol) benzyl triethyl ammonium chloride in dichloromethane (300 ml) at ice bath temperature was added 24.5 gm (0.104 mol) 1,1,2,2-tetrachloroethyl sulfenyl chloride. To the resulting solution was added dropwise 8.3 gm concentrated aqueous sodium hydroxide solution. The reaction mixture was stirred at 5°-6° C. for one hour, washed with water, and dried over magnesium sulfate. The solvent was removed in vacuo to give the product as a colorless solid (44.1 gm), m.p. 128°-129° C. Elemental analysis for $C_{12}H_{14}Cl_4N_2O_3S_2$ showed: %Cl, calc. 32.22, found 30.5; %S, 14.57; found, 14.3. The product is tabulated in Table I as Compound No. 6.

The compounds tabulated in Table I were prepared by procedures similar to that of Examples 1–5. The structure of each compound tabulated in Table I was confirmed by elemental analysis and nuclear magnetic resonance spectroscopy and/or infrared spectral analysis.

Example 6—Mite Control Tests

Compounds of the invention were tested for the control mites and mite eggs by the following procedure.

Pinto bean leaves were invested with two spotted-mites (*Tetramuchus urticae*). The mites were then allowed to lay eggs on the leaves. After 48 hours, the leaves were dipped into a water/acetone solution containing a small amount of a nonionic surfactant and 40 ppm of the test compound. The treated leaves were then maintained at 85° F. One day after treatment, the mortality of adult mites was determined, and seven days after treatment, the egg mortality (non-hatching eggs) was determined.

The results for the compounds found to have mite and mite egg control activity are tabulated in Table I.

Example 7—Tomato Late Blight

Compounds of the invention were tested for the control of the Tomato Late Blight organism *Phytophthora infestans conidia*. Five- to six-week-old tomato (variety Bonnt Best) seedlings were used. The tomato plants were sprayed with a 250-ppm solution of the test compound in acetone, water and a small amount of a nonionic emulsifier. The sprayed plants were then inoculated one day later with the organism, placed in an environmental chamber and incubated at 66°-68° F. and 100% relative humidity for at least 16 hours. Following the incubation, the plants were allowed to dry and then were maintained at 60–80% relative humidity for approximately 7 days. The percent disease control provided by a given test compound was based on the percent disease reduction relative to untreated check plants. The compounds giving effective control at the test concentration are tabulated in Table I.

Example 8—Tomato Early Blight

Compounds of the invention were tested for the control of the Tomato Early Blight organism, *Alternaria solani conidia*. Tomato (variety Bonny Best) seedlings of 6 to 7 weeks old were used. The tomato plans were sprayed with a 250-ppm solution of the test compound in an acetone-and-water solution containing a small amount of a non-ionic emulsifier. The sprayed plants were inoculated one day later with the organism, dried and maitained at 60–80% relative humidity for about 12 days. Percent disease control was based on the percent disease development on untreated check plants. The compounds giving effective control at the test concentration are tabulated in Table I.

Example 9—Celery Late Blight

Compounds of the invention were tested for the control of Celery Late Blight using celery (Utah) plants 11 weeks old. The Celery Late Blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°-68° F. in 100% relative humidity for an extended period of time (approximately 48 hours). Following the incubaticn, the plants were allowed to dry and then were maintained at a 60–80% relative humidity for approximately 14 days. The percent disease control provided by a given candidate toxicant is based on the percent disease reduction relative to untreated check plants. The compounds giving effective control at the test concentrations are reported in Table I.

Example 10—Powdery Mildew

The powdery mildew test was made using bean seedlings (var. Bountiful) with well-developed primary leaves. The pathogen was *Erysiphe polygoni*. The bean seedlings were sprayed with a 250-ppm solution of the test compound in an acetone-water mixture containing a nonionic emulsifier. The treated plants were inoculated one day after spray application of the test compound with the pathogen. The plants were then maintained in a greenhouse at a 60–80% relative humidity and at a temperature of 68°-70° F. The rate of infection on the leaves was made after about 10 days. The percent disease control provided by a given test compound was based on the disease reduction relative to untreated check plants. The compounds of the invention giving effective control at the test concentrations are reported in Table I.

Example 11—Botrytis cinerea control

Compound Nos. 1, 4, 5 and 7 of table I were tested for *Botrytis cinerea* control using detached, well-developed primary leaves of a 4–6 week old horsebean plant. The leaves were dipped into a 40-ppm solution of the test compound in acetone and water containing a small amount of a nonionic emulsifier, then taken out and placed in a petri plate lined with two pieces of filter paper. The leaves were allowed to dry while the filter paper was kept moist by adding water as required. The treated leaves were then inoculated with the spores of *Botrytis cinerea* fungus grown on potato. The plate was covered after inoculation and kept at 23.5° C. The filter-paper lining of the plate was kept saturated with water throughout the test. The rate of disease incidence was determined in 3 to 5 days, when the disease symptoms were fully evident on non-treated check leaves. The percentage disease control provided by the test compound was calculated as the percentage disease reduction based on the non-treated check leaves. The results are tabulated in Table I.

their degree of inhibition of mycelium growth. Each compound to be tested was dissolved in acetone to 500 ppm concentration. Paper strips were innoculated with the particular mycelium growth by covering the paper with a potato dextrose broth culture of mycelial suspension. The innoculated papers were then placed on potato dextrose agar plates and sprayed by means of a micro sprayer with the fungicidal solution. The treated paper strips were incubated at 25° C. and data is taken after 24 hours. Fungicidal activities are measured by a zone of inhibited mycelial growth from the center of the paper strip. The effectiveness of the compounds tested for fungicidal activity is reported in Table I in terms of the percent control of the fungus.

TABLE I $$R-SO_2N \begin{matrix} SCCl_2CCl_2H \\ \diagdown \\ R^1 \end{matrix}$$

| No. | R | $R^1$ | Melting Point, °C. | TLB$^a$ | PM$^b$ | CLB$^c$ | TEB$^d$ | BC$^e$ | Mite Control, % Adult | Eggs |
|---|---|---|---|---|---|---|---|---|---|---|
| 1* | φ | $CH_3OCCH_2-$ (O=) | 61–62 | — | 88 | 0 | 37 | 16* | 0 | 0 |
| 2 | (cyclohexyl) | $CH_3OCCH_2-$ (O=) | oil | 98 | 97 | — | 0 | 100 | | |
| 3 | (cyclohexyl) | $CH_2CH_3OCCH-$ OCH$_3$ | oil | 50 | 100 | — | 0 | 100 | 0 | 100 |
| 4 | $CH_3OCCH_2-$ (O=) | φ | 97–98 | 98 | 0 | — | 0 | 44* | 0 | 96 |
| 5 | φ | $CH_3OCCH_2-$ (O=) | 105–107 | 82 | 99 | 97 | — | 57* | 98 | 100 |
| 6 | φ | $(CH_3)NCCH_2-$ (O=) | 130–131 | 67 | 0 | 95 | 65 | 96 | 22 | 39 |
| 7* | $CH_3OCCH_2$ (O=) | φ | 118–119 | 83 | 0 | — | 91 | 0* | 0 | 0 |
| 8 | 4—CH$_3$φ | $CH_3OCCH_2-$ (O=) | 106–107 | 99 | 90 | 99 | 71 | 100 | 0 | 100 |
| 9 | φ | $CH_2CH_3OCCH-$ OCH$_3$ | oil | 97 | 85 | 95 | 96 | 59 | 0 | 100 |
| 10 | $CH_3OCCH_2-$ (O=) | 4—CH$_3$φ | 115–116 | — | 0 | — | 75 | 68 | 0 | 50 |
| 11 | $CH_3OCCH_2-$ (O=) | 3,5-(CF$_3$)$_2$φ | 92–93 | — | 0 | — | 44 | 48 | 0 | 39 |
| 12 | $CH_3OCCH-$ OCH$_3$ | φ | 114–116 | 99 | 29 | 97 | — | 90 | 0 | 100 |
| 13* | $CH_3OCCH$ OCH$_3$ | φ | 120–124 | 76 | 14 | 44 | — | 55 | 0 | 0 |
| 14 | $CH_3OCCH-$ OCH$_3$ | 3—CH$_3$φ— | 91–92 | 85 | 0 | 91 | 63 | 100 | 15 | 70 |

φ = phenyl
*M- 218
$^a$ = Tomato Late Blight
$^b$ = Powdery Mildew
$^c$ = Celery Late Blight
$^d$ = Tomato Early Blight
$^e$ = *Botrytis Cinerea*
*This compound is substituted with SCCL$_3$ instead of SCCl$_2$Cl$_2$H.

Example 11—Botrytis cinerea Mycelia Inhibition Test

Compound Nos. 2, 3, 6 and 8–14 of Table I were evaluated for fungicidal effectiveness against *Botrytis cinerea* by means of a mycelial inhibition test. This test is designed to measure the fungitoxic activity in terms of

What is claimed is:
1. A compound of the formula

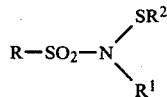

wherein R is alkyl of 1 to 6 carbon atoms; cycloalkyl of 5 to 8 carbon atoms substituted with up to 2 alkyl of 1 to 4 carbon atoms; alkoxycarbonylalkyl of 2 to 6 carbon atoms; carbamylalkyl of 1 to 6 carbon atoms; N-alkylcarbamylalkyl of 2 to 6 carbon atoms; or N,N-dialkylcarbamylalkyl of 3 to 6 carbon atoms; $R^1$ is alkyl of 1 to 6 carbon atoms; cycloalkyl of 5 to 8 carbon atoms substituted with up to 2 alkyl or 1 to 4 carbon atoms; phenyl substituted with up to 2 of the same or different substituents selected from fluoro, chloro, bromo, iodo, trifluoromethyl, trichloromethyl, tribromoethyl, or alkyl of 1 to 4 carbon atoms; alkoxycarbonylalkyl of 2 to 6 carbon atoms, carbamylalkyl of 1 to 6 carbon atoms; N-alkylcarbamylalkyl of 2 to 6 carbon atoms; or N,N-dialkylcarbamylalkyl of 3 to 6 carbon atoms; and $R^2$ is alkyl of 1 to 2 carbon atoms and of 1 to 5 fluoro, chloro, bromo or iodo atoms, with the proviso that one R or $R^1$ group is alkoxycarbonylalkyl, carbamylalkyl of 1 to 6 carbon atoms, N-alkylcarbamylalkyl of 2 to 6 carbon atoms or N,N-dialkylcarbamylalkyl of 3 to 6 carbon atoms.

2. The compound of claim 1 wherein one R or $R^1$ is alkoxycarbonylalkyl and the other R or $R^1$ is alkyl of 1 to 6 carbon atoms, cycloalkyl of 5 to 8 carbon atoms substituted with up to 2 alkyl of 1 to 4 carbon atoms or phenyl substituted with up to 2 of the same or different substituents selected from fluoro, chloro, bromo, iodo, trifluoromethyl, trichloromethyl, tribromomethyl or alkyl of 1 to 4 carbon atoms.

3. The compound of claim 1 wherein R is alkoxycarbonylalkyl and $R^1$ is phenyl substituted with up to 2 of the same or different substituents selected from fluoro, chloro, bromo, trifluoromethyl or alkyl of 1 to 4 carbon atoms.

4. The compound of claim 3 wherein R is alkoxycarbonylmethyl or 1-(alkoxycarbonyl)ethyl, and $R^2$ is trichloromethyl or tetrachloroethyl.

5. The compound of claim 2 wherein R is alkyl of 1 to 6 carbon atoms or cycloalkyl of 5 to 8 carbon atoms substituted with up to 2 alkyl of 1 to 4 carbon atoms and $R^1$ is alkoxycarbonylalkyl.

6. The compound of claim 4 wherein R is 1-(methoxycarbonyl)ethyl, $R^2$ is 1,1,2,2-tetrachloroethyl and $R^1$ is phenyl.

7. The compound of claim 4 wherein R is methoxycarbonylmethyl, $R^1$ is phenyl and $R^2$ is 1,1,2,2-tetrachloroethyl.

8. The compound of claim 4 wherein R is methoxycarbonylmethyl, $R^1$ is phenyl and $R^2$ is trichloromethyl.

9. The compound of claim 4 wherein R is methoxycarbonylmethyl, $R^1$ is 4-methylphenyl and $R^2$ is 1,1,2,2-tetrachloroethyl.

10. The compound of claim 4 wherein R is methoxycarbonylmethyl, $R^1$ is 3,5-ditrifluoromethylphenyl and $R^2$ is 1,1,2,2-tetrachloroethyl.

11. The compound of claim 4 wherein R is 1-(methoxycarbonyl)ethyl, $R^1$ is phenyl and $R^2$ is trichloromethyl.

12. The compound of claim 4 wherein R is 1-(methoxycarbonyl)ethyl, $R^1$ is 3-methylphenyl and $R^2$ is 1,1,2,2-tetrachloroethyl.

* * * * *

UNITED STATES PATENT AND TRADEMARK OFFICE
CERTIFICATE OF CORRECTION

PATENT NO. : 4,230,875
DATED : Oct. 28, 1980
INVENTOR(S) : DAVID C. K. CHAN

It is certified that error appears in the above–identified patent and that said Letters Patent are hereby corrected as shown below:

Col.1, line 7, "734,855" should read --734,858--.
Col.2, line 34, "0.2" should read --2--.

TABLE I under $R^1$ #6, "$(CH_3)\overset{\overset{O}{\|}}{N}CCH_2$"- should read --$(CH_3)_2\overset{\overset{O}{\|}}{N}CCH_2$-

Signed and Sealed this

Seventh Day of July 1981

[SEAL]

Attest:

RENE D. TEGTMEYER

Attesting Officer

Acting Commissioner of Patents and Trademarks